(12) United States Patent
Chen et al.

(10) Patent No.: US 11,116,982 B2
(45) Date of Patent: Sep. 14, 2021

(54) IMPLANTED MEDICAL DEVICE FOR USE IN TREATING ARRHYTHMIA

(71) Applicant: MICROPORT SOARING CRM (SHANGHAI) CO., LTD., Shanghai (CN)

(72) Inventors: Ningjuan Chen, Shanghai (CN); Bin Zhou, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 163 days.

(21) Appl. No.: 16/608,993

(22) PCT Filed: Apr. 28, 2018

(86) PCT No.: PCT/CN2018/085169
§ 371 (c)(1),
(2) Date: Oct. 28, 2019

(87) PCT Pub. No.: WO2018/196877
PCT Pub. Date: Nov. 1, 2018

(65) Prior Publication Data
US 2020/0139133 A1    May 7, 2020

(30) Foreign Application Priority Data
Apr. 28, 2017  (CN) .......................... 201710295897.9

(51) Int. Cl.
*A61N 1/37* (2006.01)
*A61N 1/362* (2006.01)

(52) U.S. Cl.
CPC .............. *A61N 1/37* (2013.01); *A61N 1/362* (2013.01); *A61N 1/3704* (2013.01); *A61N 1/3718* (2013.01)

(58) Field of Classification Search
CPC ........ A61N 1/37; A61N 1/3704; A61N 1/362; A61N 1/3718; A61N 1/3706; A61N 1/365; A61N 1/375
See application file for complete search history.

(56) References Cited

U.S. PATENT DOCUMENTS 4,549,548 A * 10/1985 Wittkampf ......... A61N 1/36185
607/25
4,830,006 A *  5/1989 Haluska ............... A61N 1/3621
607/12

(Continued)

FOREIGN PATENT DOCUMENTS

CN          1923312 A     3/2007
CN        101997515 A     3/2011
(Continued)

*Primary Examiner* — Catherine M Voorhees
(74) *Attorney, Agent, or Firm* — Muncy, Geissler, Olds & Lowe, P.C.

(57) ABSTRACT

The present invention relates to the field of medical devices and discloses an implantable medical device for treating arrhythmia. The implantable medical device includes a control unit and, each coupled to the control unit, a sense amplifier, a first switch and a second switch. The sense amplifier includes a polarity selection module, an amplification unit and a filtering unit, which are sequentially connected. The first switch is disposed within the polarity selection module, and the second switch within the filtering unit. The control unit is configured to shield the sense amplifier from interference from a pacing pulse signal by providing multi-stage on/off control over the first and second switches according to a pacing period and a discharging period in a pacing interval. According to embodiments of the invention, the shielding switches in the sense amplifier are switched on/off in multiple stages according to pacing and discharging periods of a pacing pulse signal so as to shield the sense amplifier from interference from the pacing pulse (Continued)

signal and enhance its pacing pulse signal suppression performance.

20 Claims, 3 Drawing Sheets

(56) References Cited

U.S. PATENT DOCUMENTS

| | | | | |
|---|---|---|---|---|
| 4,880,004 A * | 11/1989 | Baker, Jr. | ............ | A61N 1/3704 |
| | | | | 607/4 |
| 5,018,523 A | 5/1991 | Bach, Jr. et al. | | |
| 5,573,550 A | 11/1996 | Zadeh et al. | | |
| 5,873,898 A | 2/1999 | Hemming et al. | | |
| 6,112,119 A | 8/2000 | Schuelke et al. | | |
| 2003/0078627 A1 | 4/2003 | Casavant et al. | | |
| 2003/0088279 A1* | 5/2003 | Rissmann | ............ | A61N 1/3931 |
| | | | | 607/5 |
| 2016/0279430 A1* | 9/2016 | Baru | ............ | A61N 1/3727 |
| 2018/0361157 A1* | 12/2018 | Pei | ............ | A61N 1/3686 |

FOREIGN PATENT DOCUMENTS

| | | |
|---|---|---|
| CN | 202161313 U | 3/2012 |
| CN | 106474625 A | 3/2017 |
| CN | 106975153 A | 7/2017 |
| EP | 1566199 A1 | 8/2005 |
| EP | 1578492 A1 | 9/2005 |

* cited by examiner

IMPLANTED MEDICAL DEVICE FOR USE IN TREATING ARRHYTHMIA

TECHNICAL FIELD

The present invention relates to the field of medical devices and, in particular, to implantable medical devices for treating arrhythmia.

BACKGROUND

Implantable cardiac electronic devices can provide effective treatment to patients with severe arrhythmias. For such implantable electronic devices, it is important to accurately detect weak electrical signals from myocardial cells inside the heart. This may be accomplished by attaching electrodes to the endocardium so that an electrical signal can be guided, by the electrodes and leads coupled thereto, to processing circuitry within a pacemaker connected to the leads. The circuitry may include an analog front-end circuit for pre-processing the electrical signal by amplification, filtering, etc. and feeding the processed signal to a microcontroller unit (MCU), where it is determined by the MCU whether the signal is an intrinsic heartbeat signal and whether it is needed to deliver a therapeutic pacing pulse.

In the cardiac pacemaker, the key component is a heartbeat monitoring module, also known as a sense amplifier, which contains the analog front-end circuit responsible for performing amplification, filtering and other pre-processing steps on an incoming signal before it is digitized. The pacemaker relies on the sense amplifier to detect weak electrical signals from the heart, amplify R-waves, attenuate and suppress T-waves and far-field R waves, electromyographic (EMG) interference signals and other interfering signals, and determine whether the amplitude of an electrical cardiac signal exceeds a threshold. Challenges in design of a sense amplifier lie in how to achieve low noise and high linearity and in how to properly protect the amplifier devices from high voltage. A pacemaker stimulates myocardial contraction by delivering pacing pulses which, however, may affect the sense amplifier, and the ability of the sense amplifier to reject interference from pacing pulses is known as its pacing pulse suppression performance.

During the development of the present invention, the inventors have recognized that sense amplifiers of traditional pacemaker senses can perform well in terms of pacing pulse suppression when operating with a bipolar sensing polarity but exhibit inferior pacing pulse suppression performance and hence low sensing sensitivities when operating with a unipolar sensing polarity, making them less suitable for atrial pacing applications. In addition, an implantable cardiac pacemaker is required to operate safely and reliably in the patient's body for about 10 years without replacement or charging unless it fails. Therefore, the battery, typically with a capacity of about 1000 mAH, must serve for up to 10 years. Given the traditional analog front-end circuits consume power on the order of milliamperes (mA), they cannot well satisfy the requirements for use in pacemaker circuitry.

SUMMARY OF THE INVENTION

Embodiments of the present invention seek to provide implantable medical devices for treating arrhythmia, in which shielding switches in a sense amplifier are switched on/off in multiple stages according to a temporal profile of pacing and discharging periods of a pacing pulse in order to shield the sense amplifier from interference from the high voltage pacing pulse and enhance its pacing pulse suppression performance.

To this end, in one embodiment of the present invention, there is provided an implantable medical device for treating arrhythmia, including a control unit and, each coupled to the control unit, a sense amplifier, a first switch and a second switch, wherein: the sense amplifier includes a polarity selection module, an amplification unit and a filtering unit, which are connected together in this order; the first switch is disposed within the polarity selection module and the second switch within the filtering unit; and the control unit is configured to shield the sense amplifier from interference from a pacing pulse by providing multi-stage on/off control over the first and second switches according to a temporal profile of pacing and discharging periods in a pacing interval.

Compared to the prior art, multiple shielding switches are added to the sense amplifier (the first switch to the polarity selection module, and the second switch to the filtering unit) in accordance with embodiments of the present invention and are switched on/off in multiple stages by the control unit in accordance with the temporal profile of the pacing and discharging periods in the pacing interval, thereby shielding the sense amplifier against interference from any pacing pulse. The first switch is configured to enable or disable a signal input path to the amplification unit, while the second switch is configured to enable or disable a signal input path to the filtering unit. Moreover, as the amplification unit is disposed upstream of the filtering unit, the first and second switches can perform multi-stage on/off control over the amplification and filtering units. This multi-stage shielding design can protect the sense amplifier and enhance the device's reliability by efficiently avoiding a misoperation in the sense amplifier resulting from a pacing pulse.

Additionally, the sense amplifier further may include a comparator coupled to the filtering unit, wherein: the filtering unit includes a low-pass filter (LPF) and a high-pass filter (HPF); the LPF has an input coupled to an output of the amplification unit and an output coupled to an input of the HPF, and the HPF has an output coupled to an input of the comparator; and the second switch is disposed at the input of the LPF.

Additionally, the comparator may be implemented as a fully differential comparator. This allows both a differential output signal of the comparator and a differential threshold voltage thereof for comparison and hence improved anti-interference capability, common mode rejection and power supply rejection ratio.

Additionally, the implantable medical device for treating arrhythmia may further including a third switch coupled to the control unit, wherein: the third switch is disposed at the input of the HPF; and the control unit is configured to shield the sense amplifier from interference from a pacing pulse by providing multi-stage on/off control over the first, second and third switches according to the temporal profile of the pacing and discharging periods in the pacing interval. By adding the third switch at the input of the HPF, better shielding against pacing pulses can be achieved.

Additionally, the control unit may be configured to turn off all the first, second and third switches prior to the beginning of the pacing period and turn them all on subsequent to the end of the discharging period.

Additionally, the control unit may be configured to simultaneously turn off all the first, second and third switches prior to the beginning of the pacing period.

Additionally, the control unit may be configured to successively turn on the first, second and third switches at intervals. This allows any of the switches to shield out the influence of any possible residual signal present in the upstream circuit portion, while avoiding the switching action of any switch (e.g., the first or second switch) from affecting the downstream circuit portion.

Additionally, the control unit may be configured for pacing control according to a temporal profile of the pacing interval including temporally-sequenced pacing, discharging, blanking and sensing periods, wherein the control unit is configured for on/off control over the third switch within the blanking period. This allows maximum shielding against interference from pacing pulses.

Additionally, the amplification unit may be able to operate at multiple gain levels, wherein the control unit is further configured to cause the amplification unit to operate at a minimum gain level during at least part of the non-sensing portion of the pacing interval and at a preset gain level during the remainder of the interval. Since lowering the gain level could significantly reduce the fluctuation resulting from residual electric charge to the sense amplifier, better shielding against pacing pulses can be achieved.

Additionally, the amplification unit may include a current mirror and an amplification transistor, the current mirror coupled to the amplification transistor, the current mirror provided with an input current on the order of nanoamperes, the current mirror outputting a current at which the amplification transistor operates, wherein the amplification unit further includes a negative feedback circuit having an input coupled to an input of the amplification unit and an output coupled to the output of the amplification unit. This allows for stable operation of the sense amplifier at extremely low power consumption and a high gain.

The present invention provides another implantable medical device for treating arrhythmia including a sense amplifier, a first switch, a second switch and a control unit, wherein: the sense amplifier includes a general input and a general output as well as a amplification unit and a filtering unit, which are connected in this order between the general input and the general output; the first switch is coupled between the general input and an input of the amplification unit; the second switch is coupled between an output of the amplification unit and an input of the filtering unit; an output of the filtering unit is coupled to the general output; and the control unit is configured to shield the sense amplifier from interference from a pacing pulse by exerting on/off control over the first and second switches in a pacing interval.

Additionally, the pacing interval nay include temporally-sequenced pacing, discharging, blanking and sensing periods, wherein the control unit is configured to turn off the first switch at a first predetermined time point preceding the beginning of the pacing period in the pacing interval and turn it on at a second predetermined time point following the end of the discharging period in the pacing interval and to turn off the second switch at a time point not earlier than the first predetermined time point and not later than the second predetermined time point and turn it on at a third predetermined time point subsequent to the turn-on time of the first switch.

Additionally, the first and second switches may be turned off at the same time point within a final portion of the sensing period of the previous pacing interval and both turned on in the blanking period of the current pacing interval.

Additionally, the sense amplifier may further include a polarity selection module connected between the general input and the input of the amplification unit, wherein: the first switch is integrated with the polarity selection module; and the first switch is coupled between the general input and an input of the polarity selection module, or between an output of the polarity selection module and the input of the amplification unit.

Additionally, a comparator may be coupled between the output of the filtering unit and the general output, with the general output being coupled to the control unit.

Additionally, the filtering unit may include a low-pass filter (LPF) and a high-pass filter (HPF), the LPF having an input that forms the input of the filtering unit, the HPF having an output that constitutes the output of the filtering unit, the LPF having an output that is coupled to an input of the HPF via a third switch, wherein the control unit is configured to turn off the third switch at a time point not earlier than the first predetermined time point and not later than the third predetermined time point and to turn it on at a fourth predetermined time point subsequent to the turn-on time of the second switch.

Additionally, the first, second and third switches may be turned off at the same time point within a final portion of the sensing period of the previous pacing interval, wherein the third switch remains off throughout the blanking period of the current pacing interval.

Additionally, the second switch may be integrated with the LPF; and/or the third switch may be integrated with the HPF.

Additionally, the amplification unit may be able to operate at multiple gain levels, wherein the control unit is further configured to cause the amplification unit to operate at a minimum gain level during at least part of the non-sensing portion of the pacing interval and at a preset gain level during the remainder of the interval.

Additionally, the amplification unit may include a current mirror and an amplification transistor, the current mirror coupled to the amplification transistor, the current mirror provided with an input current on the order of nanoamperes, the current mirror outputting a current at which the amplification transistor operates, wherein the amplification unit further includes a negative feedback circuit having an input coupled to the input of the amplification unit and an output coupled to the output of the amplification unit.

DETAILED DESCRIPTION

The above and other objectives, features and advantages of the present invention will become more apparent from the following detailed description of various embodiments of the invention when considered in conjunction with the accompanying figures. However, it will be appreciated by those skilled in the art that while many specific details are set forth in the following embodiments in order to provide the reader with a better understanding of the invention, the subject matter of this application can be practiced without these details as well as various changes and modifications to the embodiments disclosed herein.

A pacing interval of a pacemaker is defined as a time interval from the beginning of the previous pacing pulse delivery to that of the current pacing pulse delivery. A pacing interval may include a series of temporally-sequenced periods such as pacing, discharging, blanking and sensing. Although not enumerated here, different types of pacemakers may have various pacing intervals. A pacing pulse is delivered to provide a therapeutic effect by stimulating beating of heart muscles, with its amplitude generally ranging from 1 V to 5 V and sometimes reaching up to 7.5 V. When the pacing signal at such a high level directly enters a sense amplifier, it requires a long time to restore the state of the amplification unit, thus probably affecting the detection of a responsive heartbeat which may arrive in tens of milliseconds after the pacing pulse was delivered. Therefore, the amplification unit in the sense amplifier is required to return to normal operation state in tens of milliseconds after the delivery of a pacing pulse, but this may result in a temporal overlap between the preceding discharging and following blanking periods.

Figure 1:
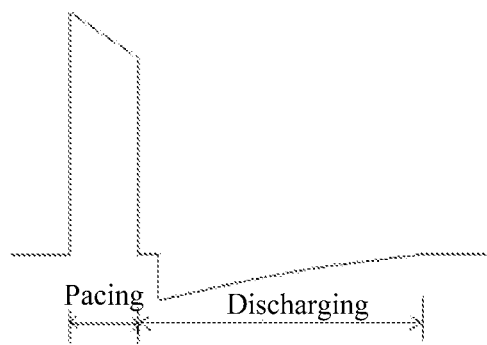
FIG. 1 is a schematic depiction of a pacing pulse delivered from a pacemaker.

FIG. 1 shows the waveform of a pacing pulse consisting of two periods: pacing and discharging. The pacing period is configured for delivering pacing pulses and spans up to 1.5 ms (milliseconds), while the discharging period corresponds to the discharging of a pacing capacitor and lasts for a longer time typically of several tens of milliseconds. The discharging may be incomplete, leaving some residual charge on the capacitor at the end of the discharging period. At the beginning of the discharging process, the electric charge on the pacing capacitor can create a voltage of up to several hundred millivolts. As the process proceeds, the voltage keeps decreasing. The longer the process lasts for, the lower the voltage will be. When the residual charge remaining from incomplete discharging migrates into the sense amplifier ("amplifier" for short) and a resulting signal is amplified therein, it may interference with a cardiac electrical signal of interest.

Figure 2:
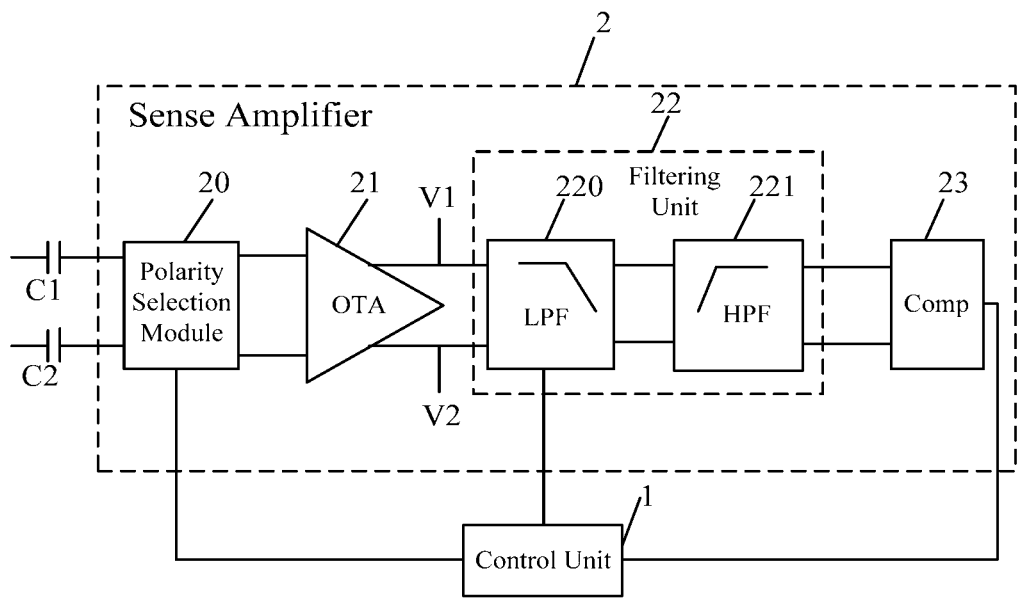
FIG. 2 is a structural schematic of an implantable medical device for treating arrhythmia according to a first embodiment of the present invention.
Figure 7:
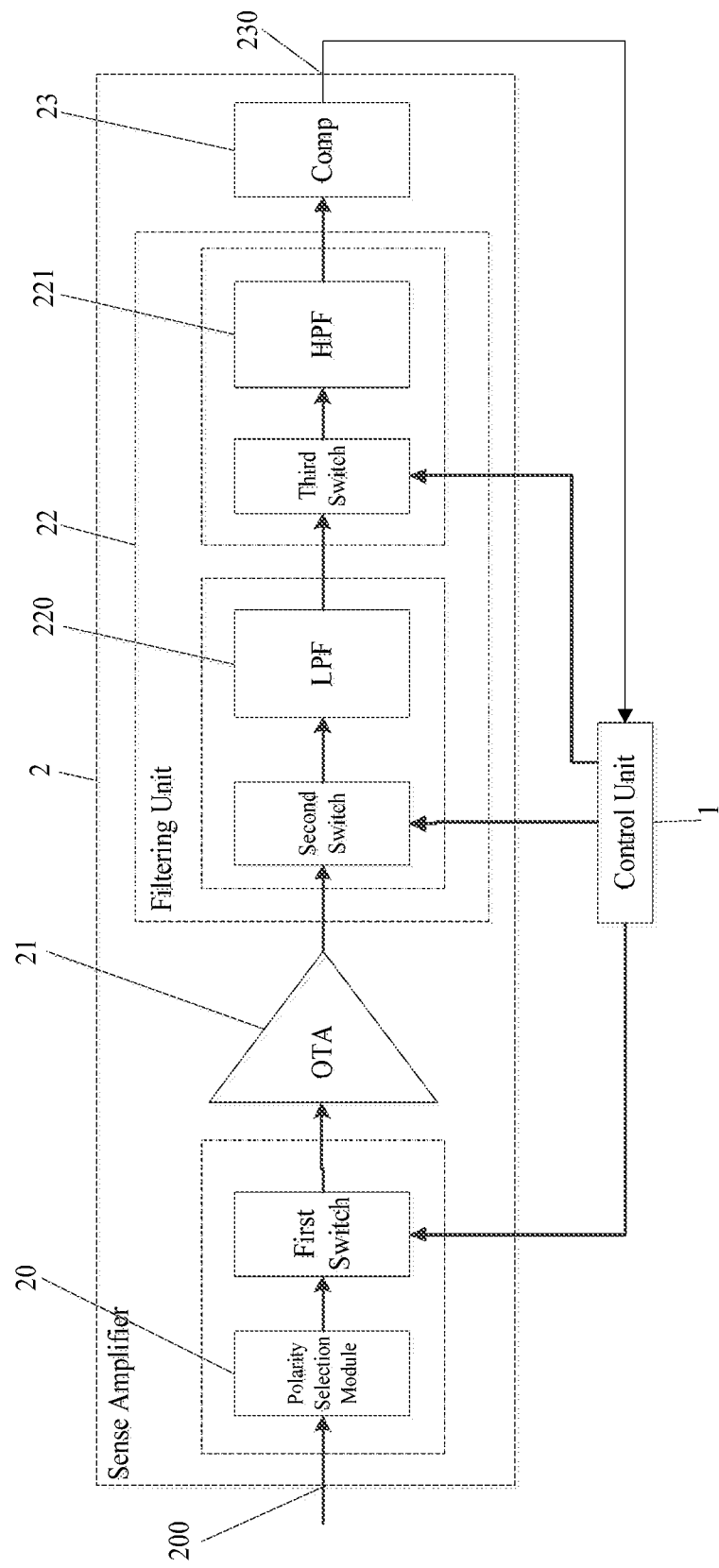
FIG. 7 is a diagram showing modules in an implantable medical device for treating arrhythmia according to an embodiment of the present invention.

A first embodiment of the present invention relates to an implantable medical device for treating arrhythmia, which is suitable for use in a pacemaker. As shown in FIG. 2, the implantable medical device for treating arrhythmia of the embodiment includes a control unit 1, a sense amplifier 2, a first switch (not shown in FIG. 2) and a second switch (not shown in FIG. 2). The sense amplifier 2 and the first and second switches are all coupled to the control unit 1. With additional reference to FIG. 7, the sense amplifier 2 has a general input 200 and a general output 230. The sense amplifier 2 includes a polarity selection (or in-switch) module 20, an amplification unit 21, a filtering unit 22 and a comparator ("Comp" for short) 23, which are connected together in this order from the general input 200 to the general output 230. The first switch is coupled between the general input 200 and an input of the amplification unit 21 (e.g., between the general input 200 and an input of the polarity selection module 20, or between an output of the polarity selection module 20 and the input of the amplification unit 21). Preferably, the first switch is disposed within the polarity selection module 20, i.e., integrated with the polarity selection module 20. The second switch is coupled between an output of the amplification unit 21 and an input of the filtering unit 22. Preferably, the second switch is disposed within the filtering unit 22. The control unit is configured to shield the sense amplifier from interference from a pacing pulse by providing multi-stage on/off control over the first and second switches according to a temporal profile of the pacing and discharging periods in a pacing interval.

For example, the input of the polarity selection module 20 may be coupled to both a first DC blocking capacitor C1 and a second DC blocking capacitor C2. The output of the polarity selection module 20 may be coupled to the input of the amplification unit 21. Preferably, the filtering unit 22 may include a low-pass filter (LPF) 220 and a high-pass filter (HPF) 221. The output of the amplification unit 21 may be coupled to an input of the LPF 220, the input of the LPF 220 is preferred to form the input of the filtering unit 22. An output of the LPF 220 may be coupled to an input of the HPF 221, while an output of the HPF 221 may be coupled to an input of the comparator 23 and the output of the HPF 221 may be preferred to constitute an output of the filtering unit 22. An output of the comparator 23 may be coupled to both the general output 230 and the control unit 1. Preferably, the second switch may be disposed at the input of the LPF 220.

The first and second DC blocking capacitors C1, C2 can filter a DC component away from an incoming cardiac electrical signal, and the filtered signal may be fed to the polarity selection module 20. The in-switch module is configured to select a sensing polarity for the sense amplifier 2, and the first switch in the in-switch module is responsible for determining whether to allow the cardiac electrical signal to enter the amplification unit 21. The amplification unit 21 may be implemented as an operational transconductance amplifier (OTA) and serve as a major contributor to the amplification of the cardiac electrical signal. The amplification unit may output an intracardiac electrogram (EGM). According to this embodiment, the sense amplifier may be of a fully differential structure capable of outputting a DC component free EGM signal that can be processed more easily by a programmer. The LPF and HPF determine the bandwidth and frequency characteristics of the sense amplifier (or known as analog front end circuit). The LPF is used mainly to filter out EMG interference, electromagnetic interference (EMI) and other high-frequency signals, while the HPF is primarily responsible for T-wave suppression. Each of the HPF and LPF may be a structure constructed from both active and passive components. The amplified and filtered analog output signal (cardiac electrical signal) may be compared with a preset threshold voltage by the comparator 23, and an output signal from the comparator, which indicates the comparison result, may be processed into a digital impulse. The control unit 1 may be further configured to determine, based on the aforesaid impulse, whether the heartbeat signal detected by the sense amplifier is higher than a sense threshold and to decide whether to deliver a therapeutic pacing pulse.

According to this embodiment, the control unit may be configured to turn off both the first and second switches prior to the pacing period and turn the first and second switches both on at the end of the discharging period. In other words, when a pulse generator of the pacemaker is not delivering any pacing pulse, the control unit is configured to turn on both the first and second switches, thereby allowing a signal to pass sequentially through the polarity selection module, the amplification unit and the filtering unit and be verified by the sense amplifier whether it is a heartbeat signal. When the pulse generator is delivering a pacing pulse, i.e., prior to the pacing period, the control unit is configured to switch off both the first and second switches. The control unit may include a microcontroller unit (MCU) and a digital-to-analog conversion (DAC) module for converting a control command from the MCU to a control signal for switching on/off the first and second switches. Specifically, the control unit can be configured to block the signal paths to the amplification and filtering units by turning off both the first and second switches and to turn on the switches successively at an interval after the end of the discharging period. That is, subsequent to the discharging period, the control unit may switch on the first switch and, tens of microseconds later, the second switch, again allowing the detection of normal heartbeat by the sense amplifier. In this way, the sense amplifier can be shielded from interference from a pacing pulse in multiple stages according to a temporal profile of the pacing and discharging periods.

Figure 3:
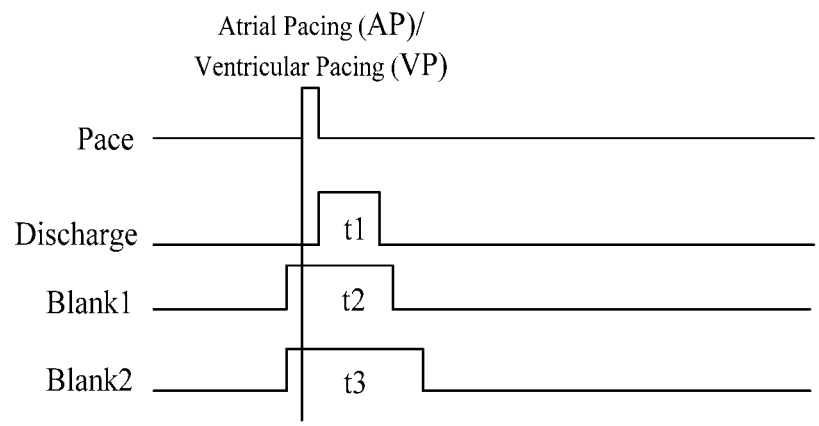
FIG. 3 is a timing diagram of on/off control over first and second switches according to the first embodiment of the present invention.

FIG. 3 is a timing diagram of on/off control over the first and second switches exerted by the control unit. As shown in FIG. 3, "Pace" is a pacing pulse delivery (i.e., pacing period) control signal that disallows pacing pulse delivery when at a low level and allows pacing pulse delivery when at a high level. "Discharge" is a discharging control signal that prevents discharging when at a low level and permits discharging when at a high level. "Blank1" is a signal for controlling the first switch in the in-switch module, when Blank1 is at a low level, the first switch is turned on and when Blank1 is at a high level, the first switch is turned off. "Blank2" is a signal for controlling the second switch disposed at the input of the LPF, when Blank2 is at a low level, the second switch is turned on and when Blank2 is at a high level, the second switch is turned off. In FIGS. 3, t1, t2 and t3 represent a discharging duration, an off-time duration of the first switch and an off-time duration of the second switch, respectively. Wherein t1, t2 and t3 satisfy t1<t2<t3. Moreover, both t2 and t3 begin tens of microseconds (preferably, not more than one hundred microseconds) earlier than t1. As can be seen from the figure, both the first and second switches have been turned off before a pacing pulse is delivered (the first switch was switched off at a first predetermined time point that before the beginning of the delivery within a final portion of the previous pacing interval's sensing period). In this way, it can be ensured that the sense amplifier is fully shielded throughout the delivery of the pacing pulse. In addition, subsequent to the expiration of the discharging period, the first and second switches are turned on successively at a time interval. The first switch is turned on at a second predetermined time point subsequent to the end of the discharging period. Preferably, the first switch is switched on in the blanking period followed by the sensing period within the pacing interval. It will be appreciated that by switching on the first switch in the blanking period, it can be turned on after the discharging period expires. The second switch can be turned on (at a third predetermined time point after the first switch is turned on) tens of microseconds later than the first switch. Preferably, the interval between the switch-on times is not longer than one hundred microseconds. This allows the switch of the next stage (i.e., the second switch) to shield out the influence of any possible residual charge of pacing pulse while avoiding the switching action of the first switch from affecting the downstream circuit portion. The embodiment does not specifically limit the time when the first switch has been described above as being turned off earlier than the beginning of the pacing period. Similarly, the embodiment does not specifically limit the time when the second switch has been described above as being turned on later than the first switch.

In practice, the sense amplifier may be configured in a unipolar sensing mode with a sensing sensitivity of 0.5 mV, a pacing pulse amplitude of 7.5 V and a pacing pulse width of 1.5 ms. At first, the programmer may configure a unipolar sensing polarity for the amplification unit, so that the pace generator of the pacemaker will generate an atrial pacing/ventricular pacing (AP/VP) pulse, which then passes through the first and second DC blocking capacitors C1, C2 shown in FIG. 2 and enters the sense amplification circuit. At a certain time (e.g., tens of microseconds, preferably not more than one hundred microseconds) before a pacing period of the pacing pulse arrives, the control unit 1 may turn off the first switch in the in-switch module to cut off the signal path to the amplification unit, and the control unit 1 may also switch off the second switch disposed at the input of the LPF 220 in order to cut off the signal path to the filter. Preferably, the switch-off time of the second switch is not earlier than the switch-off time of the first switch (the first predetermined time point) and not later than the switch-on time of the first switch (the second predetermined time point). As shown in FIGS. 1 and 3, after the expiration of the discharging period, the control unit 1 may turn off the first switch. At this point, residual electric charge on the pacing capacitor has a chance to migrate into the amplification unit 21, and a voltage signal resulting from the residual charge may be amplified by the amplification unit at the beginning of the duration t2. However, since the second switch remains off, the amplified signal from the amplification unit will not cause inversion of the comparator 23. At the end of the duration t3, the filtering unit 22 will be fully turned on to output an unrecovered signal to the comparator 23, where the signal is compared with a preset threshold. At this point, since the output signal from the filtering unit 22 is lower than the threshold voltage, the comparator 23 will not be inverted and output a low level. The comparator 23 is then digitally processed and provided to the control unit 1. Based on this, the control unit 1 determines whether a normal heartbeat or noise is detected, whether it is needed to deliver a therapeutic pacing pulse, and so on. Since interference from the pacing pulse is shielded away from the sense amplifier, the next pacing pulse delivery will not be affected.

Notably, in this embodiment, the comparator is preferred to be a fully differential comparator with four inputs. This design allows both a differential input signal of the comparator and a differential threshold voltage thereof for comparison and hence improved anti-interference capability, common mode rejection and power supply rejection ratio.

Compared with the prior art, this embodiment of the present invention adds switches (i.e., the first and second switches) respectively to the polarity selection module and the filtering unit in the sense amplifier, the first and second switches are both switched off before a pacing period of a pacing pulse arrives and are successively turned on at a time interval after a discharging period of the pacing pulse has passed. This entails multi-stage switch-on/off control which can ensure that interference from the pacing pulse is shield away from the sense amplifier, thus allowing its rapid recovery subsequent to the delivery of the pacing pulse. In the sense amplifier of this embodiment, since the amplification unit 21 is arranged in the first stage, and the LPF 220 and HPF 221 are sequentially arranged in the downstream stages, only noise in the amplification unit 21 will be amplified. Therefore, a reduction in noise in can be achieved. Moreover, in the sense amplifier, since a cardiac electrical signal passes through only one HPF with only one pole at low frequency, it will be almost not distorted at all. As a result, a distortion-free intracardiac electrogram (EGM) can be obtained, which allows the programmer to sample the cardiac electrical signal in its original, intact state.

A second embodiment of the present invention relates to an implantable medical device for treating arrhythmia. The second embodiment is modified from the first embodiment mainly in that a third switch for on/off control of the HPF 221 is further added to the filtering unit 22 in the second embodiment, which can provide the sense amplifier with better multi-stage shielding against interference from a delivered pacing pulse.

Figure 4:
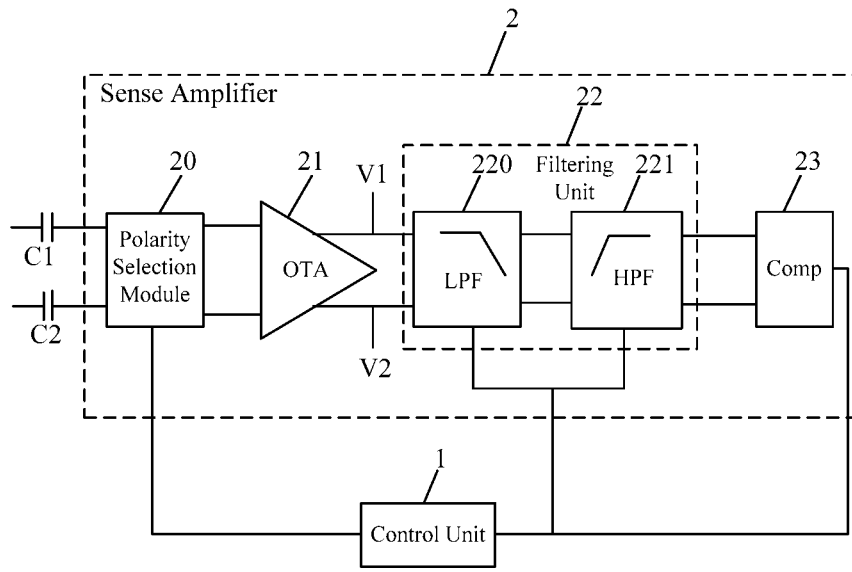
FIG. 4 is a structural schematic of an implantable medical device for treating arrhythmia according to a second embodiment of the present invention.

As shown in FIG. 4, the implantable medical device for treating arrhythmia according to this embodiment includes a control unit 1, sense amplifier 2, a first switch (not shown in FIG. 4), a second switch (not shown in FIG. 4) and a third switch (not shown in FIG. 4). The sense amplifier 2 and the first, second and third switches are all coupled to the control unit 1. The sense amplifier 2 includes a polarity selection (or in-switch) module 20, an amplification unit 21, a filtering unit 22 and a comparator 23, which are connected together in this order. The first switch is disposed inside the polarity selection module 20, the second switch at an input of an LPF 220 and the third switch at an input of an HPF 221. The third switch connects an output of the LPF 220 to the input of the HPF 221. The control unit is configured to shield the sense amplifier from interference from a pacing pulse by providing multi-stage on/off control over the first, second and third switches according to a temporal profile of the pacing and discharging periods in a pacing interval. With additional reference to FIG. 7, since this embodiment differs from the second embodiment only in additionally including the third switch, a further description of structural details of the device according to this embodiment is believed unnecessary and will be omitted here.

In this embodiment, the control unit is configured to switch off all the first, second and third switches before a pacing period of a pacing pulse arrives. For example, the first, second and third switches may be simultaneously turned off tens of microseconds before the arrival of the pacing period. The control unit is also configured to turn on all the first, second and third switches after a discharging period of the pacing pulse has passed. For example, the control unit is specifically configured to control the first, second and third switches to be turned on successively at the end of the discharging periods of the pacing pulse. Specifically, the second switch may be turned on tens of microseconds later than the first switch, and the third switch may be in turn turned on tens of microseconds (preferably, not more than one hundred microseconds) later than the second switch.

Figure 5:
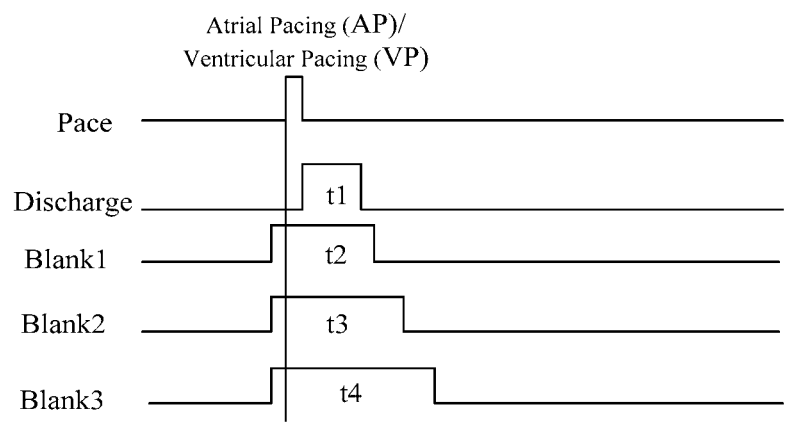
FIG. 5 is a timing diagram of on/off control over first, second and third switches according to the second embodiment of the present invention.

FIG. 5 is a timing diagram of on/off control over the first, second and third switches exerted by the control unit. As shown in FIG. 5, on the basis of the first embodiment, a signal "Blank3" is further included for controlling the third switch. The control unit is further configured for on/off control over the third switch according to the temporal profile of the pacing and discharging periods. Since the control signals "Pace", "Discharge", "Blank1" and "Blank2" function in the same way as those in first embodiment, a further description of them is believed unnecessary and will be omitted here. "Blank3" is configured to turn on the third switch when at a low level and turn off the third switch when at a high level. In the figure, t4 represents an off-time duration of the third switch, and t1, t2, t3 and t4 satisfy t1<t2<t3<t4. All of t2, t3 and t4 begin tens of microseconds (preferably, not more than one hundred microseconds) earlier than t 1 . As can be seen from the figure, the first, second and third switches have been all turned off before a pacing pulse is delivered (i.e., within a final portion of the previous pacing interval's sensing period). In this way, it can be ensured that the sense amplifier is fully shielded throughout the delivery of the pacing pulse. In addition, subsequent to the expiration of the discharging period, the first, second and third switches are turned on successively at time intervals. In particular, the third switch may be turned on tens of microseconds later than the second switch (i.e., the third switch may be turned on at a fourth predetermined time point subsequent to the switch-on of the second switch). Preferably, the interval between the switch-on times of the second and third switches is not longer than one hundred microseconds. This allows any of the switches to shield out the influence of any possible residual signal present in the upstream circuit portion, while avoiding the switching action of any switch (e.g., the first or second switch) from affecting the downstream circuit portion. However, this embodiment is not limited to any particular on/off control pattern of the first, second and third switches.

In practice, the sense amplifier may be configured in a unipolar sensing mode with a sensing sensitivity (i.e., the threshold of the comparator) of 0.5 mV, a pacing pulse amplitude of 7.5 V and a pacing pulse width of 1.5 ms. At first, the programmer may configure a unipolar sensing polarity for the amplification unit, so that the pace generator of the pacemaker will generate an AP/VP pulse, which then passes through the first and second DC blocking capacitors C1, C2 shown in FIG. 4 and enters the sense amplification circuit. At a certain time (e.g., tens of microseconds, preferably not more than one hundred microseconds) before a pacing period of the pacing pulse arrives, the control unit may turn off the first switch in the in-switch module to cut off the signal path to the amplification unit, and also switch off both the second switch disposed at the input of the LPF 220 and the third switch disposed at the input of the HPF 221 in order to cut off the signal path to the filter. Preferably, the switch-off time of the third switch is not earlier than the first predetermined time point and not later than the third predetermined time point. As shown in FIGS. 1 and 5, after the expiration of the discharging period, the control unit 1 may turn off the first switch. At this point, residual electric charge on the pacing capacitor has a chance to migrate into the amplification unit, and a voltage signal resulting from the residual charge may be amplified by the amplification unit 21 at the beginning of the duration t2. However, since the second switch remains off, the amplified signal from the amplification unit 21 will not cause inversion of the comparator 23. At the end of the duration t4, the filtering unit 22 will be fully turned on to output an unrecovered signal to the comparator 23, where the signal is compared with the preset threshold. At this point, since the output signal from the filtering unit 22 is lower than the threshold voltage, the comparator 23 will not be inverted and output a low level, the comparator 23 is then digitally processed and provided to the control unit 1. Based on this, the control unit 1 determines whether a normal heartbeat or noise is detected, whether it is needed to deliver a therapeutic pacing pulse, and so on. Since interference from the pacing pulse is shielded away from the sense amplifier 2, the next pacing pulse delivery will not be affected. Preferably, the third switch remains off during the blanking period of the pacing interval. In addition, the third switch may be turned on, for example, at the beginning of the sensing period. Of course, in other embodiments, the third switch may be alternatively turned on in a final portion of the blanking period (e.g., close to the beginning of the sensing period).

Compared with the first embodiment, each of the two filters is provided with a shielding switch in this embodiment. Through turning on the second and third switches successively at an interval, more control stages can be provided to shield the sense amplifier against interference from a pacing pulse.

A third embodiment of the present invention relates to an implantable medical device for treating arrhythmia. The third embodiment is modified from the second embodiment mainly in that the amplification unit 21 is configured to operate at different gain levels. The third embodiment further defines the gain of the amplification unit 21 in different periods of the pacing interval and thereby achieve a better shielding effect.

As noted above, a detection error may occur when a signal resulting from residual electric charge on the pacing capacitor is amplified by the amplification unit and inverts the comparator. In order to mitigate this problem, in this embodiment, the amplification unit 21 is configured by the control unit 1 to operate at a minimum gain level during at least part of the non-sensing period of the pacing interval and at a preset gain level during the remainder part of the pacing interval.

Figure 6:
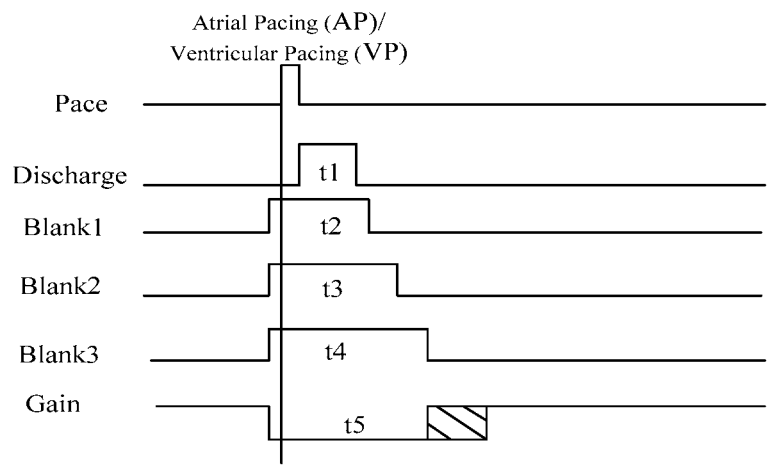
FIG. 6 is a timing diagram of gain level control over an amplification unit according to a third embodiment of the present invention.

FIG. 6 shows a timing diagram of gain level control over the amplification unit. As shown in FIG. 6, the control unit 1 may be configured to cause the amplification unit to operate at the minimum gain level during a time duration t5 and at the preset gain level during the remainder of the interval. The preset gain level may be, for example, a maximum gain level. In FIG. 6, "Gain" represents a gain level control signal for causing the amplification unit to operate at the minimum gain level when at a low electrical level and cause it to operate at the preset gain level when at a high electrical level. The amplification stage is followed by the blanking period of the pacing interval. Therefore, t5 may begin at the same time as the pacing period and end within a portion of a sensing shielding period that follows the blanking period. The sensing shielding period may begin at a certain time (e.g., tens of microseconds) earlier than the beginning of the pacing period and end at a certain time (e.g., tens of microseconds to more than one hundred microseconds) later than the end of the blanking period. In this way, when residual electric charge starts to migrate into the amplification unit at the end of t2, the amplification unit 21 is working at the minimum gain level until the control unit 1 resets the amplification unit 21 back to the preset gain level at a certain time subsequent to the passage of the discharging period of the pacing pulse. According to this embodiment, regardless of the previous value, the gain of the sense amplifier is lowered by the control unit down to the minimum value during t5 and raised back to a proper value at the end of the duration. Since lowering the gain level could significantly reduce the fluctuation resulting from the residual electric charge to the sense amplifier and the pacing pulse will almost lose its impact at the end of t5, reliability of the pacemaker can be greatly enhanced.

This embodiment is not limited to any particular time frame during which the amplification unit operates at the minimum gain level. For example, the amplification unit may alternatively operate at the minimum gain level from the beginning of the discharging period to the end of the sensing shielding period.

With this arrangement, a fluctuation level of only 10 mV will be observed at the output of the sense amplifier in response to a 7.5-V pacing pulse in a unipolar sensing mode under the worst pacing conditions, which is much lower than the threshold voltage of comparator and will not cause a detection error.

Compared with the prior art, this embodiment entails switch-based multi-stage shielding with a gain level of the amplification unit set to the minimum value during the blanking period following the delivery of a pacing pulse. This imparts significantly improved pacing pulse suppression ability to the amplifier, in particular, in a unipolar sensing mode, thereby allowing its rapid recovery in a safer, more reliable manner.

A fourth embodiment of the present invention relates to an implantable medical device for treating arrhythmia. The fourth embodiment is modified from the first, second or third embodiment mainly in the amplification unit is further able to work in a sub-threshold region in accordance with the fourth embodiment, thus lowering the pacemaker's power consumption and extend its service life.

In the implantable medical device for treating arrhythmia according to this embodiment, the amplification unit in the sense amplifier includes a current mirror and an amplification transistor coupled to the current mirror. The current mirror is provided with an input current on the order of nanoamperes and outputs a current at which the amplification transistor operates.

In regular integrated circuit (IC) chip designs, transistors in amplification units typically operate in saturation where they are fully turned on with a gate-source voltage (VGS) above the threshold voltage (VTH). Therefore, a regular chip operates at a current on the order of mA and treats a sub-threshold current as a leakage current. In contrast, since the sense amplifier in the implantable medical device for treating arrhythmia according to this embodiment operates at a frequency band up to 200 Hz, it can stably operate in a sub-threshold region. For this reason, according to this embodiment, the current mirror with an input current on the order of nanoamperes provides an operating current to the amplification transistor (for example, in case of an OTA, the input current of the current mirror is typically as low as on the order of nA and provides an operating current to each branch in the amplifier so that each transistor bias thereby operates in a sub-threshold region). As a result, the amplification unit operates at a very low current, which causes the amplification transistor to operate in a sub-threshold region, where its VGS is lower than the VTH. The current of the amplification transistor increases exponentially with the VGS, resulting in a relatively high gain of the amplification transistor. However, as the transistor has a low transconductance in the sub-threshold region, a negative feedback technique is also employed in this embodiment to ensure a high gain. Specifically, the amplification unit may further include a negative feedback circuit having an input coupled to the input of the amplification unit and an output coupled to the output of the amplification unit. The negative feedback technique can ensure that the amplification unit operates stably with a high gain.

According to this embodiment, there is only 500 nA quiescent current for atrial or ventricular amplification unit, summing to a total current of 1 uA (microampere) in the sense amplifier. Therefore, the implantable medical device for treating arrhythmia according to this embodiment consumes extremely low power.

Compared with the prior art, with the current mirroring and negative feedback techniques, the sense amplifier in the implantable medical device for treating arrhythmia according to this embodiment is capable of stable operation at extremely low power consumption and a high gain, which is favorable to an extended service life of the pacemaker.

Notably, the various modules described in connection with the foregoing embodiments are all logic modules. In practical applications, a logical module can be implemented by either a monolithic physical module or part of a monolithic physical module or by a combination of multiple physical modules. In addition, components that are not closely related to the problem sought to be solved by the disclosed embodiments are not mentioned herein in order to emphasize the inventiveness of the present invention, but this does not preclude the presence of these components in the embodiments.

Those of ordinary skill in the art will appreciate that the above embodiments are provided as specific examples for practicing the present invention and may be modified in the form and details without departing from the spirit and scope thereof.

What is claimed is:

1. An implantable medical device for treating arrhythmia, comprising a control unit as well as a sense amplifier, a first switch and a second switch each coupled to the control unit, wherein:
    the sense amplifier comprises a polarity selection module, an amplification unit and a filtering unit, which are sequentially connected;
    the first switch is disposed within the polarity selection module and the second switch is disposed within the filtering unit; and
    the control unit is configured to shield the sense amplifier from interference from a pacing pulse signal by providing multi-stage on/off control over the first and second switches according to a pacing period and a discharging period in a pacing interval.

2. The implantable medical device for treating arrhythmia according to claim 1, wherein: the sense amplifier further comprises a comparator coupled to the filtering unit;
    the filtering unit comprises a low-pass filter and a high-pass filter;
    the low-pass filter has an input coupled to an output of the amplification unit and an output coupled to an input of the high-pass filter, and the high-pass filter has an output coupled to an input of the comparator; and
    the second switch is disposed at the input of the low-pass filter.

3. The implantable medical device for treating arrhythmia according to claim 2, wherein the comparator is a fully differential comparator.

4. The implantable medical device for treating arrhythmia according to claim 2, further comprising a third switch coupled to the control unit, wherein:
    the third switch is disposed at the input of the high-pass filter; and
    the control unit is configured to shield the sense amplifier from interference from the pacing pulse signal by providing multi-stage on/off control over the first, second and third switches according to the pacing period and discharging period in the pacing interval.

5. The implantable medical device for treating arrhythmia according to claim 4, wherein the control unit is configured to turn off each of the first, second and third switches prior to a beginning of the pacing period and turn on each of the first, second and third switches subsequent to an end of the discharging period.

6. The implantable medical device for treating arrhythmia according to claim 5, wherein the control unit is configured to simultaneously turn off the first, second and third switches prior to the beginning of the pacing period.

7. The implantable medical device for treating arrhythmia according to claim 5, wherein the control unit is configured to successively turn on the first, second and third switches subsequent to the end of the discharging period.

8. The implantable medical device for treating arrhythmia according to claim 5, wherein: the control unit is configured for pacing control according to the pacing interval, which comprises, in temporal sequence, a pacing period, a discharging period, a blanking period and a sensing period; and
    the control unit is configured for on/off control over the third switch within the blanking period.

9. The implantable medical device for treating arrhythmia according to claim 1, wherein: the amplification unit is able to operate at multiple gain levels; and
    the control unit is further configured to cause the amplification unit to operate at a minimum gain level during at least part of a non-sensing period of the pacing interval and at a preset gain level during a remaining period of the pacing interval.

10. The implantable medical device for treating arrhythmia according to claim 1, wherein: the amplification unit comprises a current mirror and an amplification transistor, the current mirror coupled to the amplification transistor, the current mirror provided with an input current on an order of nanoamperes, the current mirror outputting a current at which the amplification transistor operates; and
    the amplification unit further comprises a negative feedback circuit having an input coupled to an input of the amplification unit and an output coupled to an output of the amplification unit.

11. An implantable medical device for treating arrhythmia, comprising a sense amplifier, a first switch, a second switch and a control unit, wherein:
    the sense amplifier comprises a general input and a general output as well as a amplification unit and a filtering unit, which are connected in this order between the general input and the general output;
    the first switch is coupled between the general input and an input of the amplification unit;
    the second switch is coupled between an output of the amplification unit and an input of the filtering unit;
    an output of the filtering unit is coupled to the general output; and
    the control unit is configured to shield the sense amplifier from interference from a pacing pulse signal by providing on/off control over the first and second switches in a pacing interval.

12. The implantable medical device for treating arrhythmia according to claim 11, wherein:
    the pacing interval comprises, in temporal sequence, a pacing period, a discharging period, a blanking period and a sensing period; and
    the control unit is configured to turn off the first switch at a first predetermined time point preceding a beginning of the pacing period in the pacing interval and turn on the first switch at a second predetermined time point following an end of the discharging period in the pacing interval and to turn off the second switch at a time point not earlier than the first predetermined time point and not later than the second predetermined time point and turn on the second switch at a third predetermined time point subsequent to the turn-on time of the first switch.

13. The implantable medical device for treating arrhythmia according to claim 12, wherein the first and second switches are turned off at a same time point within a final portion of the sensing period of a previous pacing interval and are both turned on in the blanking period of a current pacing interval.

14. The implantable medical device for treating arrhythmia according to claim 12, wherein:
the sense amplifier further comprises a polarity selection module connected between the general input and the input of the amplification unit;
the first switch is integrated with the polarity selection module; and
the first switch is coupled between the general input and an input of the polarity selection module, or between an output of the polarity selection module and the input of the amplification unit.

15. The implantable medical device for treating arrhythmia according to claim 11, wherein a comparator is coupled between the output of the filtering unit and the general output and the general output is coupled to the control unit.

16. The implantable medical device for treating arrhythmia according to claim 12, wherein:
the filtering unit comprises a low-pass filter and a high-pass filter, the low-pass filter having an input that forms the input of the filtering unit, the high-pass filter having an output that constitutes the output of the filtering unit, the low-pass filter having an output coupled to an input of the high-pass filter via a third switch; and
the control unit is configured to turn off the third switch at a time point not earlier than the first predetermined time point and not later than the third predetermined time point and to turn on the third switch at a fourth predetermined time point subsequent to the turn-on time of the second switch.

17. The implantable medical device for treating arrhythmia according to claim 16, wherein the first, second and third switches are turned off at the same time point within a final portion of the sensing period of the previous pacing interval and the third switch remains off throughout the blanking period of the current pacing interval.

18. The implantable medical device for treating arrhythmia according to claim 16, wherein the second switch is integrated with the low-pass filter; and/or the third switch is integrated with the high-pass filter.

19. The implantable medical device for treating arrhythmia according to claim 11, wherein: the amplification unit is able to operate at multiple gain levels; and
the control unit is further configured to cause the amplification unit to operate at a minimum gain level during at least part of a non-sensing period of the pacing interval and at a preset gain level during a remaining period of the pacing interval.

20. The implantable medical device for treating arrhythmia according to claim 11, wherein: the amplification unit comprises a current mirror and an amplification transistor, the current mirror coupled to the amplification transistor, the current mirror provided with an input current on an order of nanoamperes, the current mirror outputting a current at which the amplification transistor operates; and
the amplification unit further comprises a negative feedback circuit having an input coupled to the input of the amplification unit and an output coupled to the output of the amplification unit.

* * * * *